(12) United States Patent
Lee

(10) Patent No.: US 7,473,559 B2
(45) Date of Patent: Jan. 6, 2009

(54) **METHOD FOR MEASURING THE CONTENT OF A *BOTULINUM* TOXIN IN A FORMULATION**

(76) Inventor: Charles Lee, 3680 Wilshire Blvd., #202, Los Angeles, CA (US) 90010

( * ) Notice: Subject to any disclaimer, the term of this patent is extended or adjusted under 35 U.S.C. 154(b) by 0 days.

(21) Appl. No.: 11/400,161

(22) Filed: Apr. 5, 2006

(65) Prior Publication Data

US 2007/0237792 A1 Oct. 11, 2007

(51) Int. Cl.
*G01N 33/00* (2006.01)
*G01N 30/02* (2006.01)
*G01N 21/00* (2006.01)
*G01N 21/76* (2006.01)
*A61K 39/08* (2006.01)

(52) U.S. Cl. .................. 436/88; 436/161; 436/164; 436/172; 424/239.1; 514/844

(58) Field of Classification Search ................. None
See application file for complete search history.

(56) References Cited

FOREIGN PATENT DOCUMENTS

WO    WO 2004/074838    *    9/2004

OTHER PUBLICATIONS

Definition of bioactive: American heritage dictionary of the English language 4th edition, 2000.*
Jong-Beak et al. Infection and Immunity, Mar. 2003, p. 1147-1154.*
McMillan et al. Clinical and Experimental Dermatology vol. 7 issue 6 p. 599-604 Nov. 1982.*
Hurst et al. Biochem. J. 1999 338:723-728.*
Simonetta et al British Journal of Dermatology, 2003, 149:1041-1045.*
Murray et al. Medical Microbiology 4th edition 2002 p. 347-348.*
McMillan et al. Clinical and Experimental Dermatology, 1982, 7:599-604.*
Marincic et al. Journal of Am Diet Assoc. 1999, 99:1575-8.*
Nagasawa et al. Journal of Dairy Science 57:1159-1163.*
Simonetta et al. Br. J. Dermatol, 2003, Nov., 149:1041-1045.*
Dipietro et al. The Science of the Total Environment, 1988 vol. 74 p. 249-262.*
Manning et al. The Chemical Educator 1997, vol. 2 No. 1, Springer-Verlag NewYork, Inc.*
Jong-Beak et al. Infection and Immunity, Mar. 2003, p. 1147-1154.*
Neuenschwander et al. ENT: Ear, Nose & Throat Journal, Oct. 2000, vol. 79 Issue 10, p. 788, 9p.*
Nagasawa et al. Journal of Diary Science, 1974 57:1159-1163.*

* cited by examiner

*Primary Examiner*—Patricia A Duffy
*Assistant Examiner*—Oluwatosin Ogunbiyi
(74) *Attorney, Agent, or Firm*—Squire Sanders & Dempsey LLP

(57) ABSTRACT

A method of measuring the concentration of a bioactive agent is disclosed.

15 Claims, 1 Drawing Sheet

METHOD FOR MEASURING THE CONTENT OF A *BOTULINUM* TOXIN IN A FORMULATION

FIELD OF THE INVENTION

The present invention generally relates to a method of measuring a bioactive agent (e.g., Botox®) in a solution.

BACKGROUND OF THE INVENTION

In the field of medicine or cosmetics, it is often necessary to determine the content of a bioactive agent in a formulation on the site of use if the bioactive agent is of high toxicity, for example. However, determination of the exact content of a bioactive agent in a formulation can be tedious and complex.

For example, Botox® is a pharmaceutical formulation containing a *botulinum* toxin, e.g., the toxin *Clostridium Botulinum* A derived from the bacterium *Clostridium botulinum*. This formulation is administered by physicians and finds widespread use in cosmetic and therapeutic applications. The *botulinum* toxin is an extremely potent nerve agent. As such, pharmaceutical preparations contain only minute quantities of the toxin. The Botox A formulation discussed can include: 4.8 nanograms of the protein *Clostridium Botulinum* A, along with 0.50 milligrams of human serum albumin and 0.90 milligrams of sodium chloride. Due to the very small quantity of toxin found in a Botox® formulation, it would be extremely difficult to measure directly in a clinical setting. Botox® is manufactured as a dry powder in single vials containing 100 units of active toxin, where 1 unit is defined as the $LD_{50}$ in a mouse. It is stored at −5 degrees C. Before use, physicians dissolve the formulation in saline or water. The quantity of saline or water used varies between 1 and 8 mL. This results in the formation of Botox® solutions of varying concentrations. Currently there is a need for a simple device to measure the number of units of Botox® in a given volume after the Botox® powder form has been dissolved. This would allow independent verification of the potency of dissolved Botox®, which would benefit consumers (since they can compare number of units they are receiving) and assist in internal controls (a third party can verify that the appropriate amount Botox® was injected).

A direct measure of *botulinum* exists, but is complicated and expensive to use in the clinical setting. In contrast, the measurement of albumin is simple and inexpensive.

Therefore, there is a need for a simple and an accurate measurement of a bioactive agent such as Botox®.

The embodiments described below address se needs and issues.

SUMMARY OF THE INVENTION

P-Provided herein is a method of measuring the content of bioactive agent in a composition. The bioactive agent can be any bioactive agents or a drug. In some embodiments, the bioactive agent is a *botulinum* toxin, for example, *Clostridium Botulinum* A derived from the bacterium *Clostridium botulinum* in a formulation. The formulation can be solid, semisolid, or liquid formulation. A solid or semisolid formulation can be converted into a liquid formulation.

In some embodiments, the method is for determination of a *botulinum* toxin (e.g., *Clostridium Botulinum* A) in a liquid formulation. In some embodiments, the method includes the steps of:

determining a correlation between a *botulinum* toxin and an marker compound in the formulation, determining the concentration of the marker compound in the formulation, and determining the concentration of the *Clostridium Botulinum* A using the concentration of the marker compound.

In some embodiments, the marker compound can be a compound included in the formulation containing *Clostridium Botulinum* A. Such a compound can be a biologic compound, an organic compound or an inorganic compound. In some embodiments, the marker compound can be an albumin, e.g., human serum albumin (HSA) or sodium chloride.

DETAILED DESCRIPTION OF THE INVENTION

Figure 1:
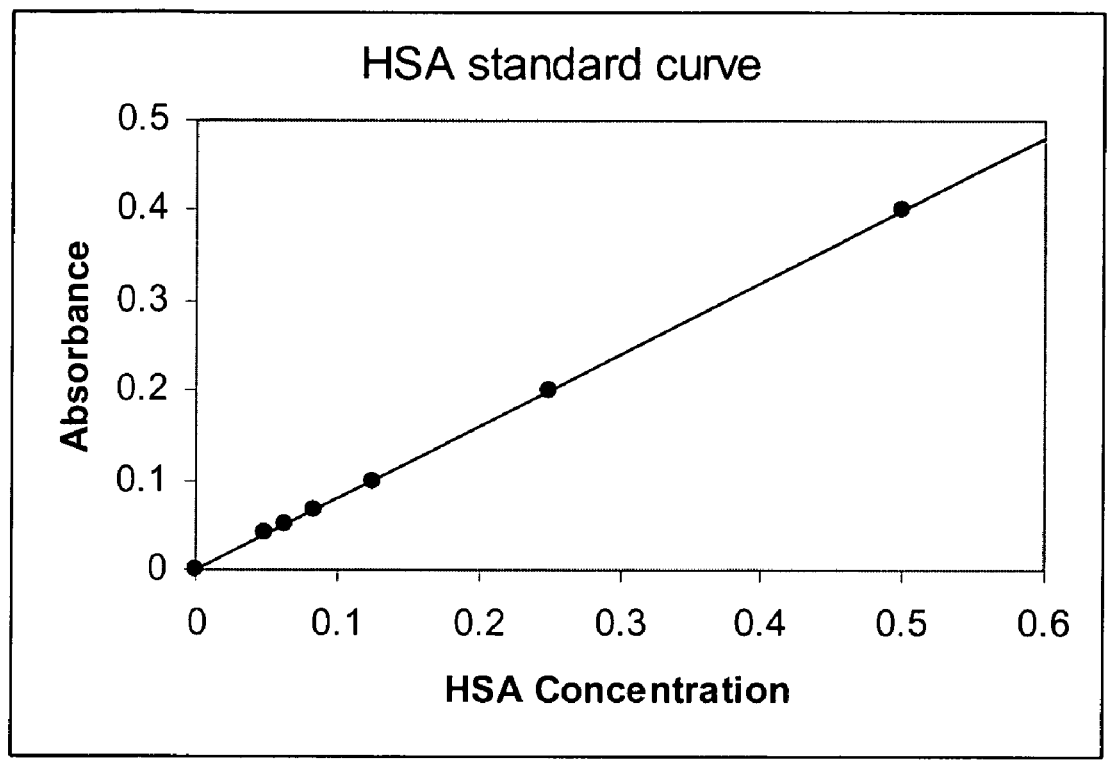
FIG. 1 shows a standard curve of HSA/bromocresol green in solution.
Figure 2:
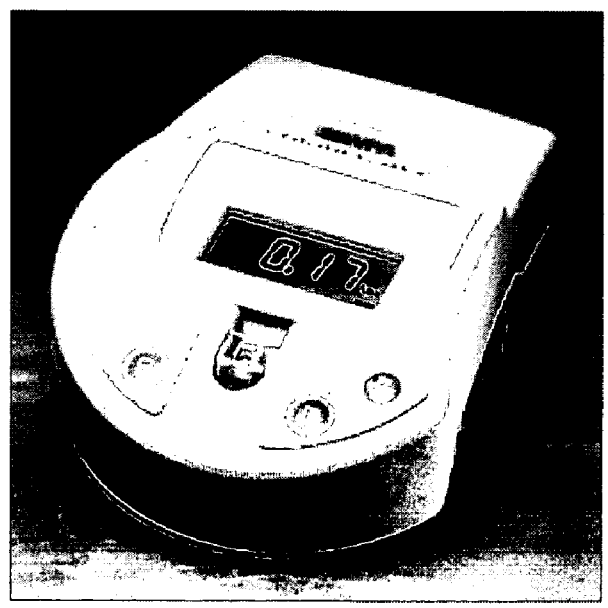
FIG. 2 shows an exemplary device for measuring HSA (Colourwave CO7000 Medical Colorimeter).

Provided herein is a method of measuring the content of bioactive agent in a composition. The bioactive agent can be any bioactive agents or a drug. In some embodiments, the bioactive agent is a *botulinum* toxin, for example, *Clostridium Botulinum* A derived from the bacterium *Clostridium botulinum* in a formulation. The formulation can be solid, semisolid, or liquid formulation. A solid or semisolid formulation can be converted into a liquid formulation.

In some embodiments, the method is for determination of the content of a *botulinum* toxin (e.g., *Clostridium Botulinum* A) in a liquid formulation. In some embodiments, the formulation can be a solid or semi-solid formulation.

In some embodiments, the method includes the steps of:

determining a correlation between *botulinum* toxin and an marker compound in the formulation, determining the concentration of the marker compound in the formulation, and determining the concentration of the *botulinum* toxin using the concentration of the marker compound.

The method described herein is applicable to the measurement of the content of any bioactive agent or drug in a formulation if such formulation includes a marker compound. As used herein, the term "marker compound" includes any biocompatible compound that can be detected and quantified by any established chemical means, physical means or biological means. Such a compound can be a biologic compound, an organic compound or an inorganic compound. In some embodiments, the marker compound can be an albumin, e.g., human serum albumin (HSA) or sodium chloride. Exemplary marker compounds include albumin (e.g., human serum albumin), sodium ion, a dye compound, or chloride ion.

Preferably, the marker compound is detectable and quantifiable by a physical means. Exemplary physical means include spectroscopy, chromatography, absorption-spectrometry, mass spectroscopy, flame atomic emission spectrometry, inductively-coupled plasma atomic emission spectroscopy, high-performance liquid chromatography, fluorescence spectroscopy, liquid-chromatography/mass-spectrometry, ultraviolet/visible spectroscopy, infrared spectroscopy, electrochemical methods using; sodium ion selective electrode, chloride ion selective electrode.

The bioactive agent, of which the content is determined by the method described herein, can be used and administered to a user according to established methods and procedures in the field of medicine and cosmetics.

Botulinum Toxin Measurement

In some embodiments, the bioactive agent is a *botulinum* toxin such as *Clostridium Botulinum* A. In the market place, *Clostridium Botulinum* A (e.g., Allergan Corporation, Irvine) is distributed to physicians in a vial of dried powder consisting of 100U of *botulinum* Type A and 500 mg of albumin and stored until ready for use. This powder is then diluted with normal saline; the recommended volume is 2.5 cc. However dilution volumes vary based on injector preference, and volumes range from 1 cc-10 cc of normal saline. The activity of *Clostridium Botulinum* A is dependent on the number of units injected; the typical amount is 6-20 units per site. *Clostridium Botulinum* A is sold on a per unit basis.

By measuring the amount of albumin content of a given solution, a simple indirect measurement of the *botulinum* toxin can be achieved. A variety of devices are currently available to measure albumin, one common method being the use of light spectrophotometry.

Human serum albumin, or HSA, is a very common blood plasma protein. It is used by the body as a carrier for water-insoluble molecules. In Botox®, it is included in the formulation to transport the *botulinum* toxin. Albumin may be measured directly using relatively inexpensive equipment. Since there is a large, consistent quantity of HSA in each *botulinum* toxin formulation (e.g., Botox® formulation), HSA can serve as a direct indicator of the quantity of toxin present in a *botulinum* toxin formulation (e.g., a Botox® solution) of unknown concentration.

In some embodiments, the content of the *botulinum* toxin (e.g., *Clostridium Botulinum* A) can be determined by the detection or measurement of the content of sodium ion ($Na^+$) in the *botulinum* toxin formulation (e.g., a Botox® formulation). The *botulinum* toxin formulation contains an amount of sodium chloride. For example, some Botox® formulation can include 4.8 nanograms of the protein *Clostridium Botulinum* A, along with 0.50 milligrams of human serum albumin and 0.90 milligrams of sodium chloride. Accordingly, by measuring the amount of sodium ion, one can determine the quantity of the *botulinum* toxin. Sodium ion content can be determined by sodium ion selective membrane or flame photometry, for example.

All other marker compounds (e.g., chloride ion) can be detected and measured by established method and procedures (see, e.g., Handbook of Instrumental Techniques for Analytical Chemistry, Frank A. Settle, Ed., Prentice Hall, 1997; Vogel's Quantitative Analysis ($6^{th}$ Edition), J. Mendham, Ed., Prentice Hall, 2000).

EXAMPLES

Example 1

Indirect Measurement of *Clostridium Botulinum* A via HSA Measurement

This example describes the use of albumin as an indirect measurement of the number of Botox units in a given volume. This covers all *botulinum* toxin constitutions containing albumin (currently *Clostridium Botulinum* A (Allergan Corp); Dysport (Ipsen, Ltd), Myobloc (Solstice Neuroscience, Inc)). Each of the components in the formulation (the toxin, albumin, and salt) is found in exacting quantities and therefore the ratios of each are consistent from one vial to the next.

In solution, HSA binds quantitatively with organic dyes such as bromocresol green. The binding between the HSA and dye results in the formation of a blue/green colored solution. Under standard conditions, the intensity of the solution color is directly proportional to the concentration of HSA present in solution.

The concentration of HSA/dye solution may be determined using an inexpensive visible spectrophotometer or colorimeter using a wavelength of 630 nm. This spectroscopic method follows Beer's Law, where the absorbance is equal to the products of extinction coefficient ($\epsilon$), concentration (c), and path-length (b), or A=$\epsilon$bc. Since $\epsilon$ and b are constants, absorbance is directly proportional with concentration.

Equipment

The equipment necessary to perform the above described measurements can be both inexpensive and common. There are three basic pieces of equipment required: an instrument, such as a pipette, to measure a precise volume of sample to be tested, a cuvette, or test tube in which to measure the absorbance of the solution, and a visible spectrophotometer, or colorimeter to measure absorbance. There are several manufacturers of spectrophotometers and colorimeters, one example of which is Colourwave CO7000 Medical Colorimeter (available from Isogen Benelux, The Netherlands).

A typical standard curve for determining HSA concentration is shown in FIG. 1. Plots, such as this one, may be used to extrapolate the concentration of HSA in an unknown solution, simply by adding a standard quantity of a dye to a small portion of a sample and then measuring the absorbance of the solution at a fixed wavelength.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of determining the concentration of a bioactive agent in a pharmaceutical formulation comprising a bioactive agent, comprising:
   determining a correlation between the bioactive agent and a marker compound in the formulation by deriving a ratio of the bioactive agent to the marker compound in the formulation,
   measuring the concentration of the marker compound in the formulation, and
   determining the concentration of the bioactive agent using the concentration of the marker compound and the ratio of the bioactive agent to the marker compound,
   wherein the bioactive agent is a *botulinum* toxin, and
   wherein the marker compound is selected from the group consisting of albumin, and human serum albumin.

2. The method of claim 1, wherein the marker compound is albumin.

3. The method of claim 1, wherein the marker compound is human serum albumin (HSA).

4. The method of claim 1, wherein the marker compound is detected by high-performance liquid chromatography, fluorescence spectroscopy, liquid-chromatography/mass-spectrometry, ultraviolet/visible spectroscopy.

5. The method of claim 1, wherein the bioactive agent is *Clostridium Botulinum* toxin A.

6. The method of claim 2, wherein the bioactive agent is *Clostridium Botulinum* toxin A.

7. The method of claim 3, wherein the bioactive agent is *Clostridium Botulinum* toxin A.

8. The method of claim 4, wherein the bioactive agent is *Clostridium Botulinum* toxin A.

9. The method of claim 1, wherein the formulation is a liquid formulation.

10. The method of claim 3, wherein the formulation is a liquid formulation.

11. The method of claim 4, wherein the formulation is a liquid formulation.

12. A method of providing cosmetic treatment using a *botulinum* toxin, comprising:
    determining the content of the *botulinum* toxin in a formulation according to the method of claim 1,
    providing an amount of *botulinum* toxin according to the content determined according to the determining step, and
    administering to a user the amount of the *botulinum* toxin in the formulation.

13. A method of providing cosmetic treatment using a *botulinum* toxin, comprising:
    determining the content of the *botulinum* toxin in a formulation according to the method of claim 3,
    providing an amount of *botulinum* toxin according to the content determined according to the determining step, and
    administering to a user the amount of the *botulinum* toxin in the formulation.

14. The method of claim 12, wherein the *botulinum* toxin is *Clostridium Botulinum* A.

15. The method of claim 13, wherein the *botulinum* toxin is *Clostridium Botulinum* A.

\* \* \* \* \*